United States Patent
Bose et al.

(10) Patent No.: US 10,531,613 B2
(45) Date of Patent: Jan. 14, 2020

(54) METHOD AND A CONTAINER FOR EFFECTING AT LEAST ONE NON-LETHAL CHANGE IN INHERENT PROPERTIES OF A NON-HUMAN BIOLOGICAL SYSTEM UNDER THE INFLUENCE OF ZERO GRAVITY

(71) Applicant: Airbus DS GmbH, Taufkirchen (DE)

(72) Inventors: Guido Bose, Immenstaad (DE); Andreas Grasl, Rordrof/Thansau (DE)

(73) Assignee: AIRBUS DS GMBH, Taufkirchen (DE)

( * ) Notice: Subject to any disclaimer, the term of this patent is extended or adjusted under 35 U.S.C. 154(b) by 549 days.

(21) Appl. No.: 15/348,385

(22) Filed: Nov. 10, 2016

(65) Prior Publication Data

US 2017/0142909 A1    May 25, 2017

(30) Foreign Application Priority Data

Nov. 19, 2015  (DE) .......................... 10 2015 222 880

(51) Int. Cl.
*A01G 7/04* (2006.01)
*A01G 18/00* (2018.01)

(52) U.S. Cl.
CPC .............. *A01G 7/04* (2013.01); *A01G 18/00* (2018.02)

(58) Field of Classification Search
CPC ..................................................... A01G 7/04
See application file for complete search history.

(56) References Cited

U.S. PATENT DOCUMENTS

| 3,822,505 A | 7/1974 | Levengood |
| 4,891,317 A | 1/1990 | Brown, Jr. |
| (Continued) | | |

FOREIGN PATENT DOCUMENTS

| DE | 3027604 | 2/1982 |
| DE | 10151974 | 4/2003 |
| (Continued) | | |

OTHER PUBLICATIONS

German Search Report, dated Jun. 21, 2016, priority document.
(Continued)

*Primary Examiner* — Kristen C Hayes
(74) *Attorney, Agent, or Firm* — Greer, Burns & Crain, Ltd.

(57) ABSTRACT

A container for effecting at least one non-lethal change in inherent properties of a non-human biological system, such as a plant or a fungus, under the influence of zero gravity, comprising a carrier plate configured to receive two capacitor plates of a plate capacitor, wherein the plates are situated parallel to one another and in each case perpendicularly on the carrier plate, at least one sample container arranged horizontally on the carrier plate, adjacent to each of the two capacitor plates and configured to receive the biological system, and an electromagnet arranged substantially half way between the capacitor plates and, when seen from the carrier plate, arranged horizontally above the at least one sample container. Additionally, a European modular cultivation system for use in the International Space Station comprises a centrifuge, wherein the container is received in the centrifuge.

13 Claims, 6 Drawing Sheets

(56) References Cited

U.S. PATENT DOCUMENTS

| | | | |
|---|---|---|---|
| 5,740,627 A * | 4/1998 | Levengood | A01C 1/00 47/1.3 |
| 5,888,791 A | 3/1999 | Ebner | |
| 6,539,664 B2 | 4/2003 | Katsen et al. | |
| 2003/0069464 A1 * | 4/2003 | Muntermann | A61N 2/02 600/13 |
| 2013/0225908 A1 * | 8/2013 | Jacobson | A61N 2/02 600/13 |
| 2018/0133467 A1 * | 5/2018 | Wald | A61N 1/086 |

FOREIGN PATENT DOCUMENTS

| | | | |
|---|---|---|---|
| EP | 0197748 | 10/1986 | |
| EP | 0351357 | 1/1990 | |
| EP | 0791651 | 8/1997 | |
| WO | WO-2016107750 A1 * | 7/2016 | A61B 5/0515 |

OTHER PUBLICATIONS

"Exploration of plant growth and development using the European Modular Cultivation System facility on the International Space Station" Kittang A., 2014.

"Plant biology in reduced gravity on the Moon and mars", Kiss J.Z., 2014.

Experiment Container (EC) User Handbook. DOC.: EMCS-MA-4000-002-DOR.

Master Thesis of Axel Schoen, Johannes Gutenberg Universität Mainz, 2001 "Auswirkungen elektrostatischer Felder auf das Keimverhalten und die Ontogenie verschiedener Getreidearten".

* cited by examiner

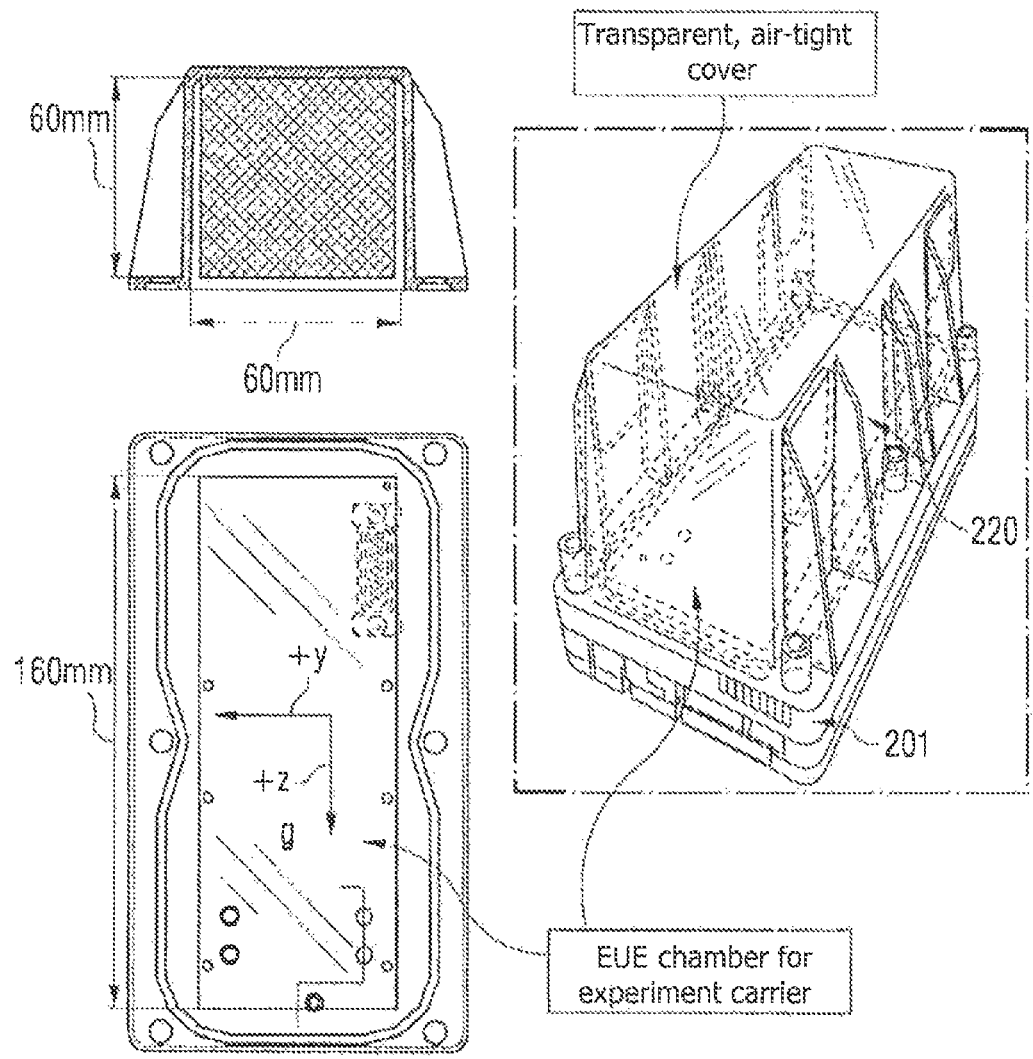

METHOD AND A CONTAINER FOR EFFECTING AT LEAST ONE NON-LETHAL CHANGE IN INHERENT PROPERTIES OF A NON-HUMAN BIOLOGICAL SYSTEM UNDER THE INFLUENCE OF ZERO GRAVITY

CROSS-REFERENCES TO RELATED APPLICATIONS

This application claims the benefit of the German patent application No. 10 2015 222 880.0 filed on Nov. 19, 2015, the entire disclosures of which are incorporated herein by way of reference.

FIELD OF THE INVENTION

The present invention relates to a method and a container for effecting at least one non-lethal change in inherent properties of a non-human biological system, in particular of a plant or of a fungus, under the influence of zero gravity.

The invention relates, in particular, to the application of electrostatic voltage under zero gravity conditions, for example within the International Space Station (ISS), on the basis of scientifically proven studies for demonstrating the influence of an electrostatic field on plants, which exhibit a change in relation to morphological development and gene expression. These applications have hitherto been demonstrated on earth under conventional environmental conditions; in the present invention, the influence of, for example, zero gravity, magnetism, increased gravity, ionized air, and increased radiation, is applied in various arrangements.

BACKGROUND OF THE INVENTION

As early as the 1980s, various electrostatic experiments were carried out with plants and animal tissue samples within an electrostatic field. Surprisingly, unexpected reactions thereby occurred, which could not be explained scientifically at first. Cress can be used as an example here; in the experiment it was stressed by, for example, removing the light in the electric field. Nevertheless, the cress developed in the electric field without adverse effects. Germination and growth, in particular, were even boosted in the electric field.

An original form of plants and organisms existed during the Jurassic and Cretaceous period from 230-65 million B.C. At that time, gigantism was predominant among the biological systems, giant plants (e.g., ferns) and giant saurians populated the earth. The reason for the gigantism at that time has not yet been researched. One possible reason could be increased electrostatic voltage in the environment, as a result either of climatic influences or of more intensive tectonic plate shifts.

A test arrangement 100 for this purpose is shown in FIG. 1. A sample vessel or seed tray 103 containing, for example, samples or plant seedlings P (e.g., in test tubes or Petri dishes) is placed between two capacitor plates 101, 102. An electrostatic field is generated between the plates of the capacitor. The electric field strength is calculated by the voltage difference between the capacitor plates divided by the distance between the plates. The required voltage difference between the capacitor plates is generated by a high voltage generator 104.

According to some specific modifications, spores, seeds or microbes, as desired, can be placed in this E field. They are removed therefrom again after a specific time, for example after germination, and transferred to their natural environment, where they are allowed to flourish. Such a simple experimental setup, such an astonishing effect: In many cases, a type of original form of the original plants and organisms, as described above, is obtained in this manner. It was as though certain genetic information, which had been inactivated in the course of evolution, spontaneously became active again in the next generation. Moreover, germination and growth were boosted in the E field, as described above.

This experimental setup can also be performed, for example, with "halophile" (salt-loving) bacteria from the Red Sea. Astonishing discoveries were likewise made in this experiment: the microorganisms of the genus "*Halobacterium balobium*" which were colonized in a conventional nutrient-rich common salt solution multiplied as expected scientifically; however, if the clear solution was exposed to an electric field for eight to fourteen days, the liquid turned blood-red, to general astonishment. The reason for this was identified as being increased production of rhodopsin as a pigment, caused by the E field.

In a further experiment it was proved that stress situations are actually overcome better under the action of an E field; green algae cultivated in Petri dishes were used as an example. Result: the cultures without the E field showed significant changes after only one month and turned brown after a further month. The algae in the E field, on the other hand, did not show any damage during the same period.

Experts agree that the effects observed upon application of a specific static E field are causally connected and are not based on any other, uncontrollable factors.

In the earth's atmosphere, too, there is a natural E field, which has changed in the past in terms of its strength. It is therefore likely that the earth's E field also had an influence on gene expression, that is to say on the transmission of the information of the individual genes and thus on the evolution of life.

Scientifically Proven Morphological Changes

It has further been found that adult plants grown from seeds which were germinated under the above-described conditions in the static electric field in some cases exhibited morphological changes as compared with the control plants. These changes related to:
  increased biomass (10-100%)
  yield increase (30-120%)
  greatly accelerated growth
  resistance to bacteria and resistance to environmental influences
  increased reproduction and improved seed
  stalks with more ears or cobs (wheat and maize)
  changed phyllotaxy
  formation of panicles with a large number of ears and cobs
  bushing forms, creeping forms
  larger ears, larger cobs
  greater number of grains

EXPERIMENTAL ARRANGEMENTS AND EXAMPLES

Example of an Experimental Setup for Watercress Performed Under Laboratory Conditions Watercress was likewise investigated within the scope of an E field project. In each case 140 cress seeds were made to germinate with water in two Petri dishes on filter paper. One dish was thereby exposed to an electric field of 750 V/cm. The negative plate of the capacitor formed the lid of the test cell. Because the germination of the seeds is greatly influenced by light, the experiment was carried out in the conventional manner under standardized light conditions, in this case in a darkroom, the interior of which was illuminated by a 100 Watt plant light at a distance of 29 centimeters from the surfaces of the experiment cells.

Result: The rate of germination in the electric field was 83 percent. In the blank experiment without a static E field, on the other hand, on average only 21 percent of the same number of seeds germinated. Subsequent sowing in soil in daylight showed that all the seeds were equally germinable. However, the seeds in the E field grew more quickly and exhibited a changed habitus—they had smaller leaves and longer stems.

Garden Cress

Example of an Experiment with Garden Cress

An exact number of cress seeds (140 per test batch) was distributed on filter paper in Petri dishes; 5 ml of water was added, and the dishes were sealed with paraffin. One of the Petri dishes was introduced into the above-described experimental arrangement during the germination phase (about 5 days) and was there exposed to a strong static electric field with field strength values of 750 V/cm. The negatively charged plate of the capacitor formed the lid of the experiment cell. The second Petri dish remained outside the range of influence of the static electric field and served as control. In order to exclude an uncontrolled influence of the light on germination, the experiment was here too carried out under standardized light and temperature conditions in a darkroom, the interior of which was illuminated by a 100 Watt plant light at a distance of 18 cm from the surfaces of the experiment cells. The temperature in the darkroom was between 23° C. and 24° C.

The rate of germination of the cress seeds used was determined after the hypocotyls and the cotyledons had developed. For the seeds germinated in the static electric field, it was 83% in the mean. In the blank experiment without a static electric field, on the other hand, only on average 21% of the same number of seeds germinated. Subsequent sowing out in soil in daylight showed that all the seeds were equally germinable. This experiment was likewise carried out with wheat and maize and fish spawn and showed astonishing results.

SUMMARY OF THE INVENTION

The present invention strives for a method and a container for effecting at least one non-lethal change in inherent properties of a non-human biological system, in particular of a plant or of a fungus, under the influence of zero gravity.

In a first aspect there is provided a method for effecting at least one non-lethal change in inherent properties of a non-human biological system, in particular of a plant or of a fungus, under the influence of zero gravity, comprising the steps of introducing the biological system into an electrostatic field, setting parameters of the electrostatic field, subjecting the biological system to a factor which includes at least one of artificial gravity and magnetic field, setting parameters of the factor, and leaving the biological system in the electrostatic field and under the influence of the factor until the at least one non-lethal change is achieved.

In a first form of the first aspect, when the factor is artificial gravity, the gravity is preferably set at a constant or variable value between 0 g and 2 g. The gravity is preferably set by controlling a centrifuge.

In a second form of the first aspect, when the factor is the magnetic field, the magnetic field is set at a constant or variable value between 20 $\mu T$ and 100 $\mu T$.

In a second aspect there is provided a container for effecting at least one non-lethal change in inherent properties of a non-human biological system, in particular of a plant or of a fungus, under the influence of zero gravity, comprising a carrier plate which is configured to receive two capacitor plates of a plate capacitor, wherein the plates are situated parallel to one another and in each case perpendicularly on the carrier plate, at least one sample container which is arranged horizontally on the carrier plate, is adjacent to each of the two capacitor plates and is configured to receive the biological system, and an electromagnet which is arranged substantially half way between the capacitor plates and, when seen from the carrier plate, is arranged horizontally above the at least one sample container.

In a first form of the second aspect, the electromagnet generates a magnetic field and is preferably configured to set the magnetic field at a constant or variable value between 20 $\mu T$ and 100 $\mu T$.

In a second form of the second aspect, one of the two capacitor plates is preferably in the form of a perforated plate.

In a third form of the second aspect, the container preferably comprises a planar mirror which is arranged above the electromagnet and is inclined relative to the carrier plate.

In a fourth form, the container is preferably an experiment standard container, EC, and the carrier plate is preferably a customized experiment-unique equipment, EUE, carrier plate, wherein the EC and the EUE are preferably designed for use in zero gravity.

In a third aspect there is provided a European modular cultivation system, EMCS, for use in the International Space Station, ISS, which comprises a centrifuge, wherein a container according to the second aspect is received in the centrifuge.

In a first form of the third aspect, the centrifuge is preferably configured to set an artificial gravity with a constant or variable value between 0 g and 2 g.

BRIEF DESCRIPTION OF THE DRAWINGS

The accompanying drawings show embodiments of the invention, to which the present invention is not, however, to be limited in any way. In the drawings, the same reference numerals denote the same or similar constituent elements. It should be noted that the representation of individual constituent elements does not exclude the possibility that the particular underlying functionality in question can be implemented in a plurality of elements. In the drawings:

FIG. 4 is a top view, a side view and a perspective view of an empty container according to the invention.

DETAILED DESCRIPTION OF THE PREFERRED EMBODIMENTS

In the following description, specific details are described, for the purposes of explanation but not of limitation, in order to ensure a fundamental understanding of the technology presented herein. It is clear to the average person skilled in the art that the present technology can be realized in other embodiments which depart from these specific details.

Figure 1:
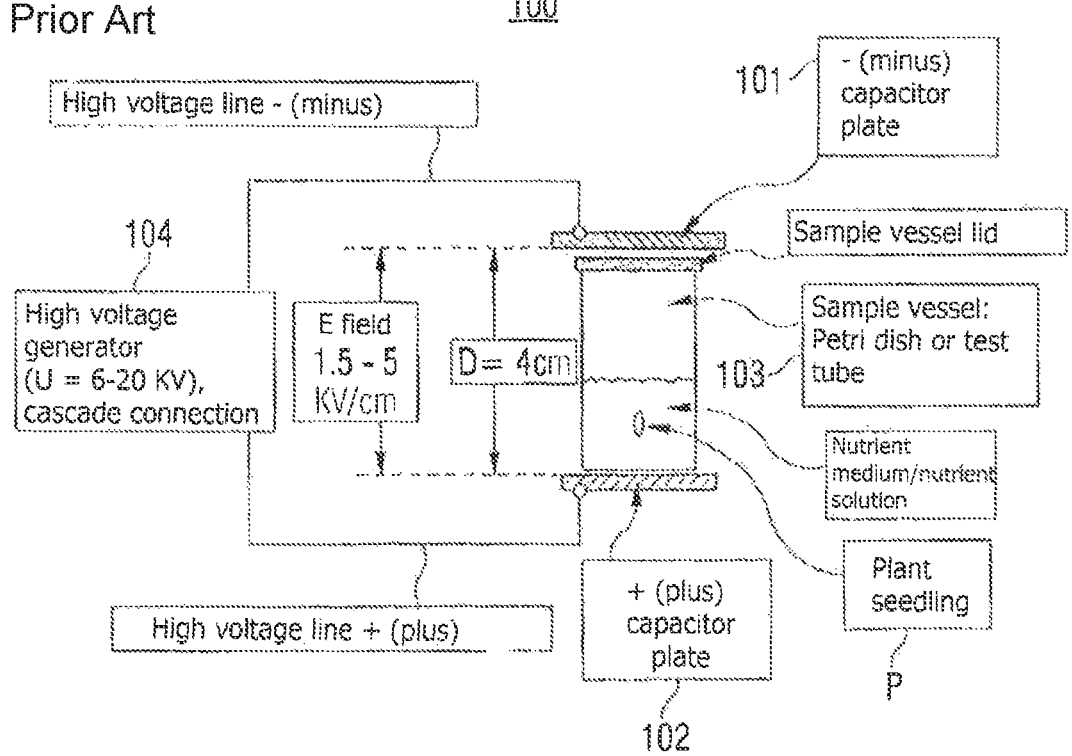
FIG. 1 shows the arrangement of the system according to the prior art.
Figure 2:
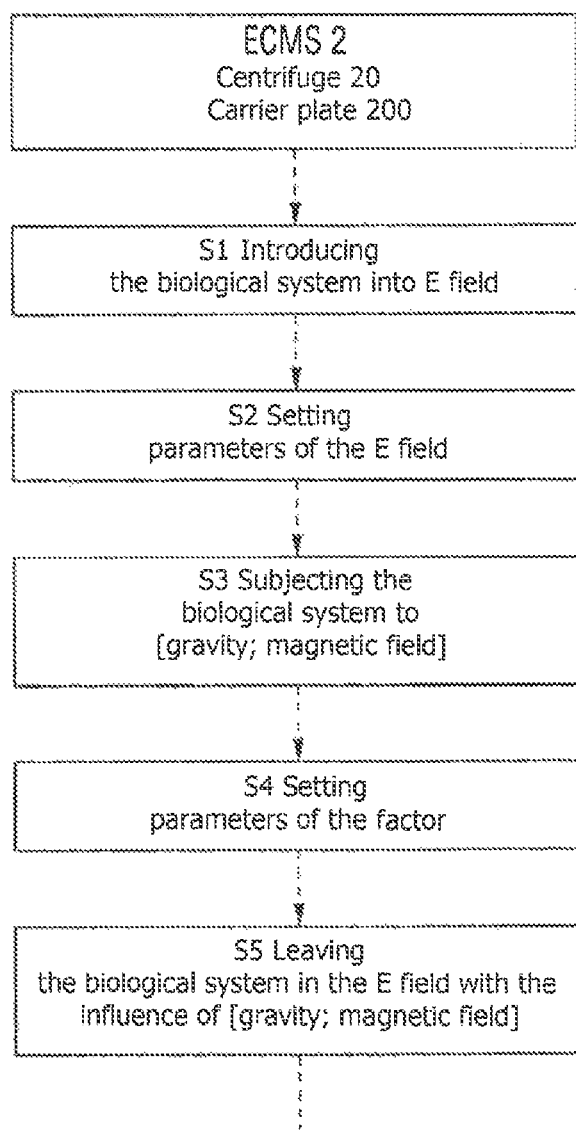
FIG. 2 shows a method according to the present invention.

FIG. 2 shows a method according to the present invention for effecting at least one non-lethal change in inherent properties of a non-human biological system (in particular of a plant or of a fungus) under the influence of zero gravity. It is clear to the person skilled in the art that the method steps, provided they do not depend on one another, can also be carried out simultaneously or in a different order.

In a first step S1, the biological system is introduced into an electrostatic field, and in a step S2, the parameters of the electrostatic field (E field) are set. The person skilled in the art is hereby expected to perform several series of experiments until the suitable parameter setting for a desired effect (e.g., gigantism) has been calculated; conversely, it is likewise conceivable to choose a given parameter and evaluate the effect that is achieved.

In a step S3, the biological system is subjected to a factor which includes at least one of artificial gravity and magnetic field, and in a step S4, the parameters of the factor are set. Here too, the person skilled in the art is expected to perform several series of experiments until the suitable parameter setting for a desired effect (e.g., gigantism) has been calculated; conversely, it is likewise conceivable to choose a given parameter and evaluate the effect that is achieved.

Finally, in a step S5, the biological system is left in the electrostatic field and under the influence of the factor until the at least one non-lethal change is achieved. In this connection, the electrostatic field generated in the subject-matter of the invention can bring about a certain ionization of the ambient air. However, if results or circumstances show that an even greater degree of ionization is necessary to produce desired changes, corresponding measures can be taken, such as, for example, supplying ionized air or additionally fitting an ionizer.

Figure 3:
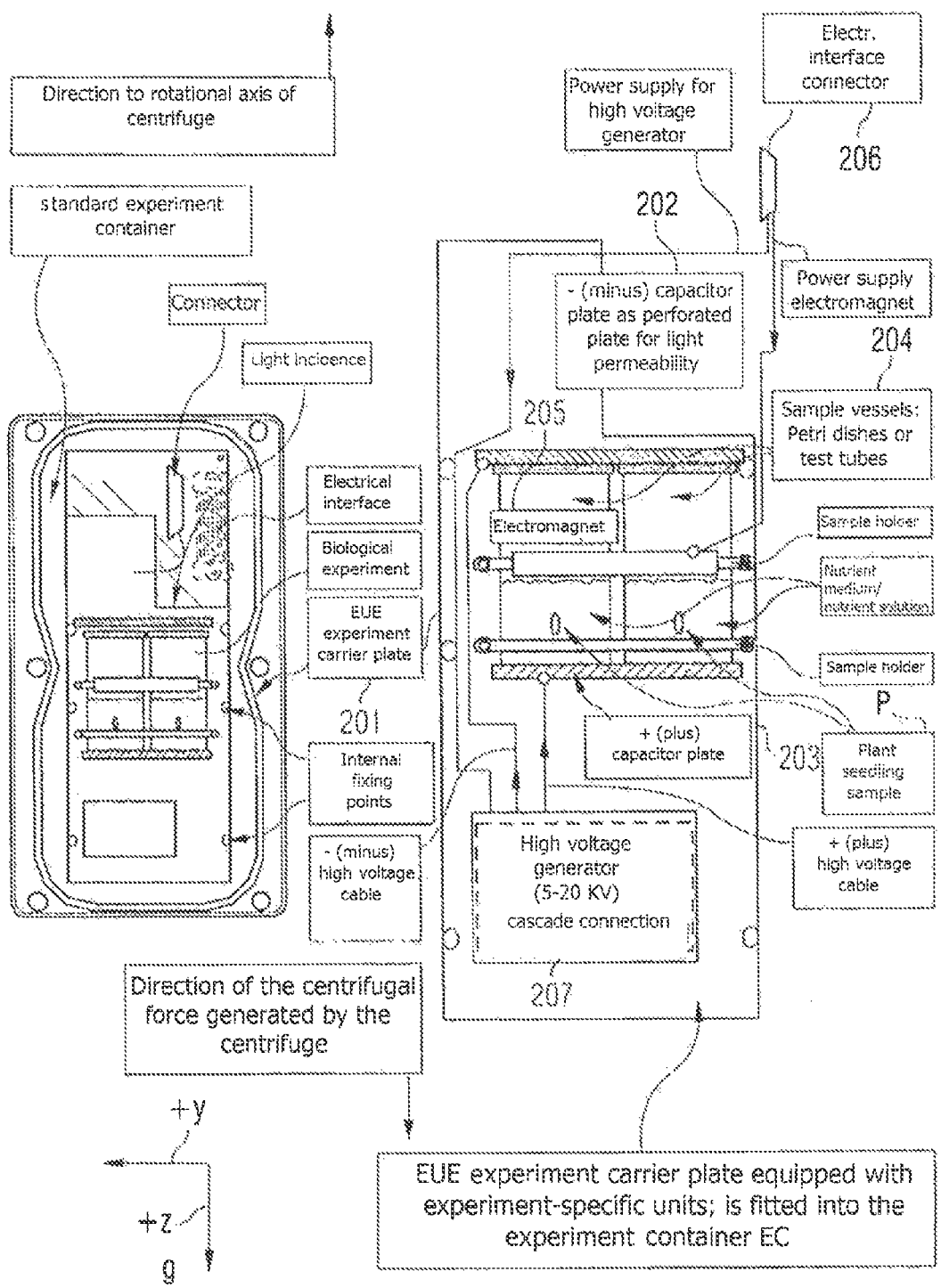
FIG. 3 is a top view of the implementation of an arrangement within a container according to the invention.
Figure 3A:
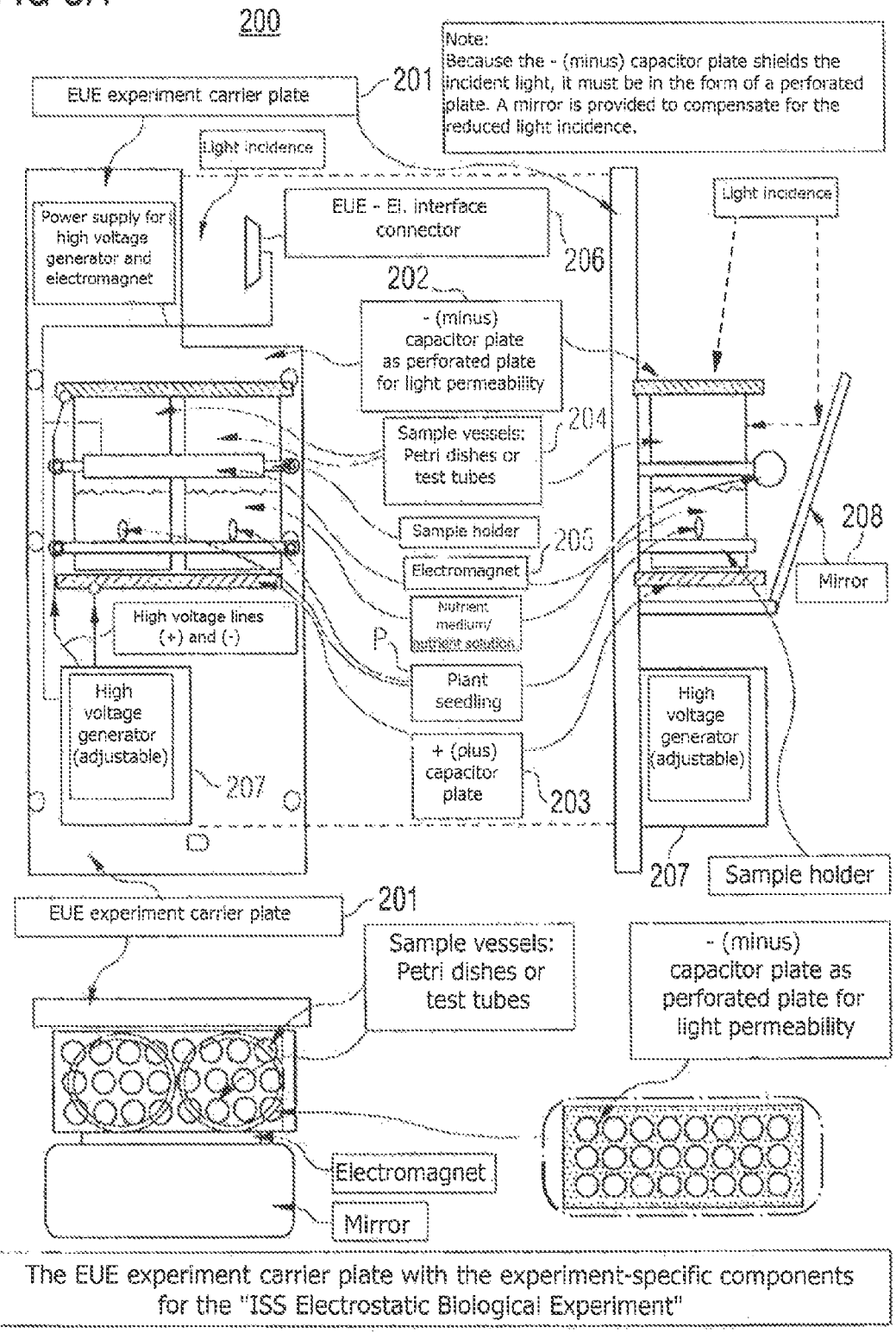
FIG. 3A is a top view and two side views of the implementation of the arrangement of the container according to the invention.

FIG. 3 shows a top view of the implementation of an arrangement within a container according to the invention, FIG. 3A shows a top view and two side views of the implementation of the arrangement of the container according to the invention, and FIG. 4 shows a top view, a side view and a perspective view of an empty container according to the invention.

The container 200 serves to effect at least one non-lethal change in inherent properties of a non-human biological system P, in particular of a plant or of a fungus, under the influence of zero gravity. To that end, the container 200 comprises a carrier plate 201, a first (e.g., negatively charged) capacitor plate 202 of a plate capacitor, a second (e.g., positively charged) capacitor plate 203 of the plate capacitor, at least one sample container 204, an electromagnet 205, an external power supply 206, a high voltage generator 207 and a planar mirror 208.

The carrier plate 201 is configured to receive the two capacitor plates 202, 203 of the plate capacitor, wherein the plates are situated parallel to one another and in each case perpendicularly on the carrier plate. The at least one sample container 204 is arranged horizontally on the carrier plate, is adjacent to each of the two capacitor plates and is configured to receive the biological system. Finally, the electromagnet 205 is arranged substantially half way between the capacitor plates 202, 203 and, when seen from the carrier plate, is arranged horizontally above the at least one sample container 204.

All the experiments described in the following use the experimental setup described above and are to be carried out in static electric fields, which are generated between the plates 202, 203 of the capacitor. The electric field strength is given by the following equation: $E=U/d$, where U denotes the voltage difference between the capacitor plates and d denotes the distance between the plates of the capacitor. The necessary DC voltage is generated by means of the high voltage generator 207 (e.g. transformer principle with downstream rectifier or, preferably, cascade connection).

The distance between the plates of the capacitor is governed by the dimensions of the sample vessels 204 used in the individual experiments. According to experience of previous tests, the variable parameters "U" and "d" are so chosen that the static electric field preferably has field strength values between 500 V/cm and 5000 V/cm. Furthermore, previous experiments have shown that it is beneficial to position the negative voltage in the direction of the fruit of the plant and the positive voltage in the region of the roots; however, this does not rule out the possibility of a reverse polarity being present.

The intensity of the light necessary for growth, sufficient moisture and sufficient nutrient solution is to be chosen for each experiment, for example according to ISS standards/experience. However, this does not exclude the possibility that these basic parameters can be verified or optimized during the experiments.

Performing biological experiments on the ISS

No biological experiments with electrostatic and magnetic stimuli have hitherto been performed in the ISS European modular cultivation system (EMCS) facility. The concept of "performing biological experiments on the IS S" is therefore a novelty and fits well into the flexible use of EMCS. The concept provides for fitting, for example, into an EMCS experiment container. In principle, this is to be regarded as technically feasible. Miniaturization of the power supply can also be considered. The use of the subject-matter of the invention in EMCS with variable gravity acceleration is possible within the scope of nominal use. Preliminary and subsequent treatment (e.g. watering, fixing or harvest) are likewise to be taken into consideration in the design or in the operational sequence. The subject-matter of the invention can also be used for manned long-term missions (see keywords: exploration, food production).

Figure 5:
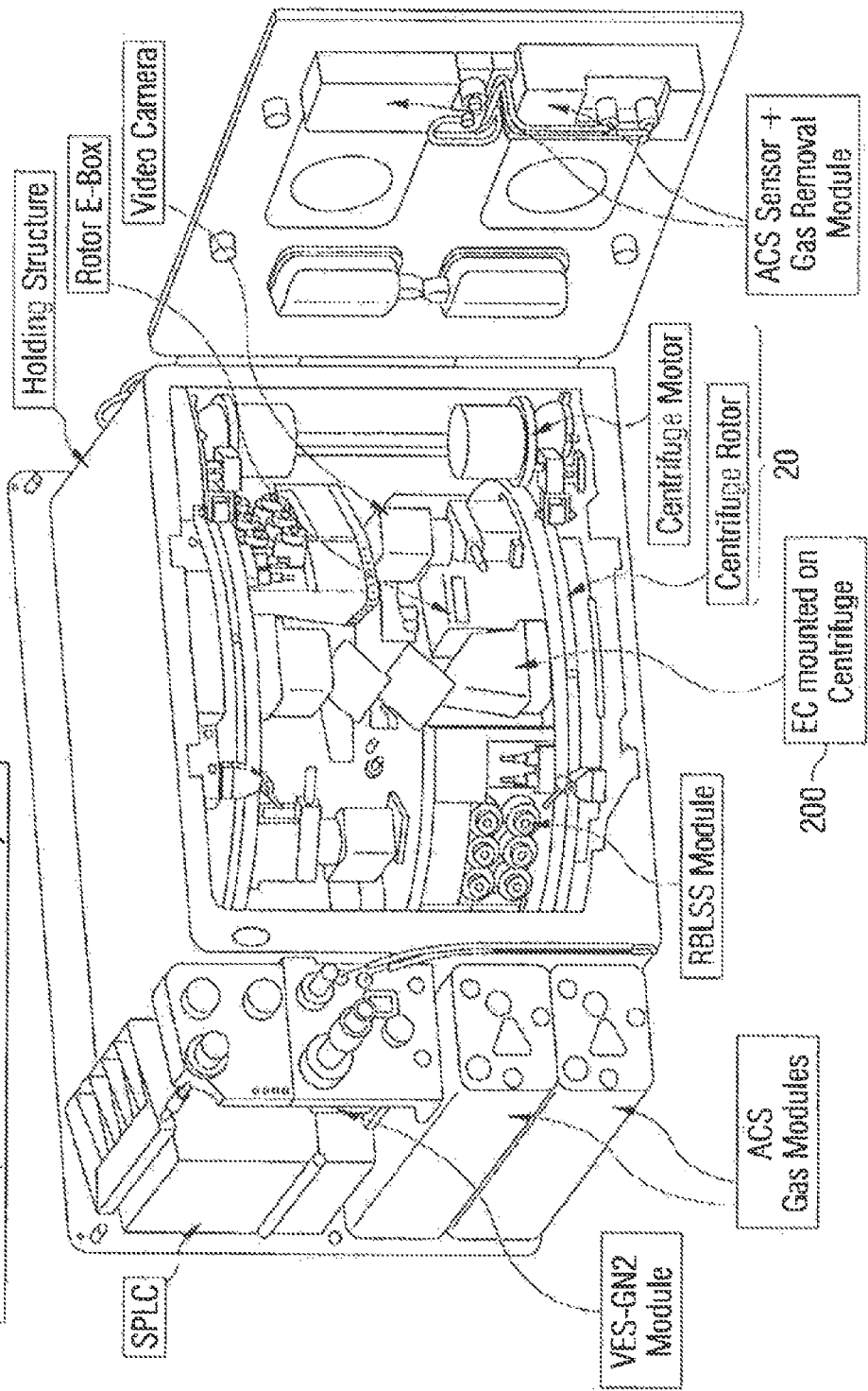
FIG. 5 is a perspective view of an EMCS having a centrifuge in which the container according to the invention is received.

On the ISS (as a particular form of a zero gravity environment, without implying any limitation), the EMCS "European modular cultivation system" 2, which is shown in FIG. 5, is available for performing biological experiments. This is an ESA experiment system which provides ambient conditions, such as temperature, light, humidity, and also a variable gravity of from 0 g to 2 g in a centrifuge 20.

For performing the experiments, "standard experiment containers" (EC) are available (which form an embodiment of the container, without implying any limitation), into which customer-specific experiment carriers, so-called "customized experiment-unique equipment" (EUE, which can be an embodiment of the carrier plate 201 with superstructures, without implying any limitation) can be fitted (see Experiment Container (EC) User Handbook. DOC.: EMCS-MA-4000-002-DOR).

The whole of the specific setup (EUE), as is necessary for carrying out the invention, is to be installed inside this "standard equipment container" (EC).

It includes:
- the sample vessels 204, such as, for example, Petri dishes, test tubes, or sample vessels permitted according to ISS standard (see reference numeral 204 in FIG. 3) etc.
- optionally nutrient solutions or nutrient media in the sample vessels
- sample holders
- the high voltage generator 207 (preferably in cascade connection)
- the capacitor plates 202, 203 with associated cabling to the generator 207
- optionally the (electro)magnet 205 for (variable) simulation of an (increased) terrestrial magnetic field
- sensor systems and cabling to the electrical interface connector
- optionally ionizers for air ionization
- optionally the planar mirror 208 for optimizing light incidence due to perforated (-) capacitor plate The experiment container (EC) is a container which, as mentioned above, provides the user with an "experiment chamber" of dimensions 60×60×160 mm3 (see FIG. 4). Special experiments can be installed in this standard container via the EUE. These are preferably carried out in the EUE.

In other words, the standard EC comprises the carrier plate 201 and a cover 220 which in the fitted state provides an enclosed air-tight chamber (60×60×160 mm3) for experimental samples and/or the EUE. The EUE can be fixed mechanically to the carrier plate 201 and can be provided with a water and gas exchange through openings in the carrier plate while it is in the centrifuge. The experiment can be illuminated through the surface (which is opposite the z axis in FIG. 4) with a transparent cover.

FIG. 5 shows a perspective view of an EMCS 2 with a centrifuge 20 in which the container 200 according to the invention is received. In one embodiment, the EC (container 200) with the specific measuring setup EUE (carrier plate 201 with associated superstructure) is preferably fitted into the "EMCS Incubator 2 with at least one centrifuge," as shown in FIG. 5.

The centrifuge is preferably configured to set an artificial gravity with a constant or variable value between 0 g and 2 g.

Optimization of experimental parameters and ambient parameters

By application of the invention and by means of the results obtained, the following experimental parameters of the experimental setup can be optimized:
- range of the optimum field strength (V/cm) in relation to the treated plants, fungi, etc.
- polarization of the electrostatic voltage field; positive voltage in the region of the roots and negative voltage in the region of the fruits or vice versa?

Furthermore, by application of the invention, the influence of the following ambient parameters on the growth and the development or desirable and useful changes of plants, fungi or other biological forms in the electrostatic field can be investigated and optimized:
- zero gravity
- gravity below 1 g, e.g., Martian gravity simulation with about 0.4 g
- 1 g gravity
- 2 g gravity
- simulated increased terrestrial magnetism
- ionized air
- cosmic radiation (intensity regulated by shielding)

Variations of different combinations should be investigated

A further approach could comprise allowing a biological sample (plant seedling) to germinate in a 2 g gravity field and an electrostatic field and investigating the extent to which "inactivated genetic information" would activate, for example, a "more intense growth energy" through the electrostatic field and the increased gravity field, as compared with the increased gravity to which the sample (plant seedling) is now exposed. This could be determined if, after the germination phase, the sample so treated was planted out either in zero gravity or in a 1 g terrestrial or a 0.4 g Martian gravity field.

A further approach could comprise allowing a biological sample (plant seedling) to germinate in a magnetic field that is increased compared with the prevailing terrestrial magnetic field (B field) and an E field and investigating whether "inactivated genetic information" would activate a "more intense growth energy" through the increased magnetic field. The prevailing terrestrial magnetic field is 20-40 µT. The electromagnet 205, which is mounted close to the sample (plant seedling) and through the coil of which there flows variable current, can influence the sample with a variable magnetic field of 20-100 µT.

A further approach would comprise investigating the possible activation of "inactivated genetic information" by a combination of electrostatic voltage, simulated, increased magnetic field, increased gravity, optionally increased ionization of the ambient air and optionally regulated cosmic radiation.

The invention offers the following advantages inter alia:

The applications described above are essential and of great importance for biological science, agricultural science and medical science. The present invention builds on this proven research with broadened parameters; this means introducing into the arrangements, in addition to the electrostatic field, further parameters such as zero gravity, microgravity, increased gravity, or increased terrestrial magnetism, in order to investigate expected desirable and beneficial changes in plants, fungi or other biological forms and to obtain for the future useful and validated agricultural, medical, reproductive and biological knowledge. This also provides knowledge and preparations for future terraforming The applications described above also include parameters of ionized air or increased radiation (in order to investigate radiation resistance) and their effect on the plant seedlings, fungi, etc.

In terms of further prospects, it would be interesting for medicine to know to what extent penicillin fungi, for example, can be regressed by the gene expression effect, for example in order to identify current penicillin resistance in humans and produce a new form of penicillin with a correspondingly new fungus. This means that the current penicillin fungus could be regressed back to the "original fungus" by the static electric experiment in order to identify a difference between today's fungus and the fungus of that time; this could allow a new fungus to be produced which does not cause resistance in humans.

The subject-matter of the invention can also be used for manned long-term missions (see keywords; exploration, food production).

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A container for effecting at least one non-lethal change in inherent properties of a non-human biological system, under the influence of zero gravity, comprising:
    a carrier plate configured to receive two capacitor plates of a plate capacitor, wherein the plates are situated parallel to one another and in each case perpendicularly on the carrier plate;
    at least one sample container arranged horizontally on the carrier plate, arranged adjacent to each of the two capacitor plates and being configured to receive the biological system; and
    an electromagnet arranged substantially half way between the capacitor plates and, when seen from the carrier plate, is arranged horizontally above the at least one sample container.

2. The container according to claim 1, wherein the electromagnet generates a magnetic field and is configured to set the magnetic field at a constant or variable value between 20 µT and 100 µT.

3. The container according to claim 1, wherein one of the two capacitor plates is in the form of a perforated plate.

4. The container according to claim 1, further comprising:
    a planar mirror arranged above the electromagnet and inclined relative to the carrier plate.

5. The container according to claim 1, wherein the container is an experiment standard container EC and the carrier plate is a customized experiment-unique equipment EUE carrier plate, wherein the EC and the EUE are designed for use in zero gravity.

6. The container according to claim 1, wherein the non-human biological system comprises a plant or a fungus.

7. A European modular cultivation system EMCS for use in the International Space Station, comprising:
    a centrifuge, a container for effecting at least one non-lethal change in inherent properties of a non-human biological system, under the influence of zero gravity, comprising:
        a carrier plate configured to receive two capacitor plates of a plate capacitor, wherein the plates are situated parallel to one another and in each case perpendicularly on the carrier plate;
        at least one sample container arranged horizontally on the carrier plate, arranged adjacent to each of the two capacitor plates and being configured to receive the biological system; and
        an electromagnet arranged substantially half way between the capacitor plates and, when seen from the carrier plate, is arranged horizontally above the at least one sample container,
    wherein the container is received in the centrifuge.

8. The EMCS according to claim 7, wherein the centrifuge is configured to set an artificial gravity with a constant or variable value between 0 g and 2 g.

9. The EMCS according to claim 7, wherein the electromagnet generates a magnetic field and is configured to set the magnetic field at a constant or variable value between 20 µT and 100 µT.

10. The container according to claim 7, wherein one of the two capacitor plates is in the form of a perforated plate.

11. The container according to claim 7, further comprising:
    a planar mirror arranged above the electromagnet and inclined relative to the carrier plate.

12. The container according to claim 7, wherein the container is an experiment standard container EC and the carrier plate is a customized experiment-unique equipment EUE carrier plate, wherein the EC and the EUE are designed for use in zero gravity.

13. The container according to claim 7, wherein the non-human biological system comprises a plant or a fungus.

* * * * *